(12) United States Patent
Doyle et al.

(10) Patent No.: US 6,872,194 B2
(45) Date of Patent: Mar. 29, 2005

(54) DISPOSABLE SELF-SHIELDING SYRINGE GUARD

(75) Inventors: Mark Christopher Doyle, San Diego, CA (US); Lars Tommy Westbye, Carlsbad, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 0 days.

(21) Appl. No.: 10/062,683

(22) Filed: Jan. 31, 2002

(65) Prior Publication Data

US 2003/0144631 A1 Jul. 31, 2003

(51) Int. Cl.[7] .................................................. A61M 5/32
(52) U.S. Cl. ...................................... 604/192; 604/198
(58) Field of Search ........................... 604/192, 195, 604/196, 197, 198, 199, 200, 201, 218, 232, 234, 235, 264, 164.01, 162, 163, 111, 181, 187, 263

(56) References Cited

U.S. PATENT DOCUMENTS

| | | | | |
|---|---|---|---|---|
| 5,242,416 A | * | 9/1993 | Hutson | 604/192 |
| 5,372,590 A | | 12/1994 | Haber et al. | |
| 5,562,624 A | * | 10/1996 | Righi et al. | 604/110 |
| 5,762,635 A | * | 6/1998 | Pace et al. | 604/195 |
| 6,461,333 B1 | * | 10/2002 | Frezza | 604/192 |

FOREIGN PATENT DOCUMENTS

| | | |
|---|---|---|
| WO | WO 99/17823 A1 | 4/1999 |
| WO | WO 01/80931 A2 | 11/2001 |

* cited by examiner

*Primary Examiner*—Long V. Le
*Assistant Examiner*—Ann Y. Lam
(74) *Attorney, Agent, or Firm*—Orrick, Herrington & Sutcliffe, LLP

(57) ABSTRACT

A guard for a syringe that includes a needle, a needle protector cap, and a barrel with an outer diameter smaller than the needle protector cap. The guard includes a body having a cavity for receiving the syringe therein, and a shield that is slidable between an unguarded position wherein the needle is exposed and a guarded position covering the needle. One or more tabs in a wall of the body are deflectable from a first position wherein the tabs extend along the wall or radially outwardly from the wall, to a second position wherein the tabs are directed inwardly into the cavity for contacting the barrel of the syringe. In other embodiments, a collar or other radial element may be provided on the barrel of the syringe to provide lateral support within the cavity of the body.

11 Claims, 16 Drawing Sheets

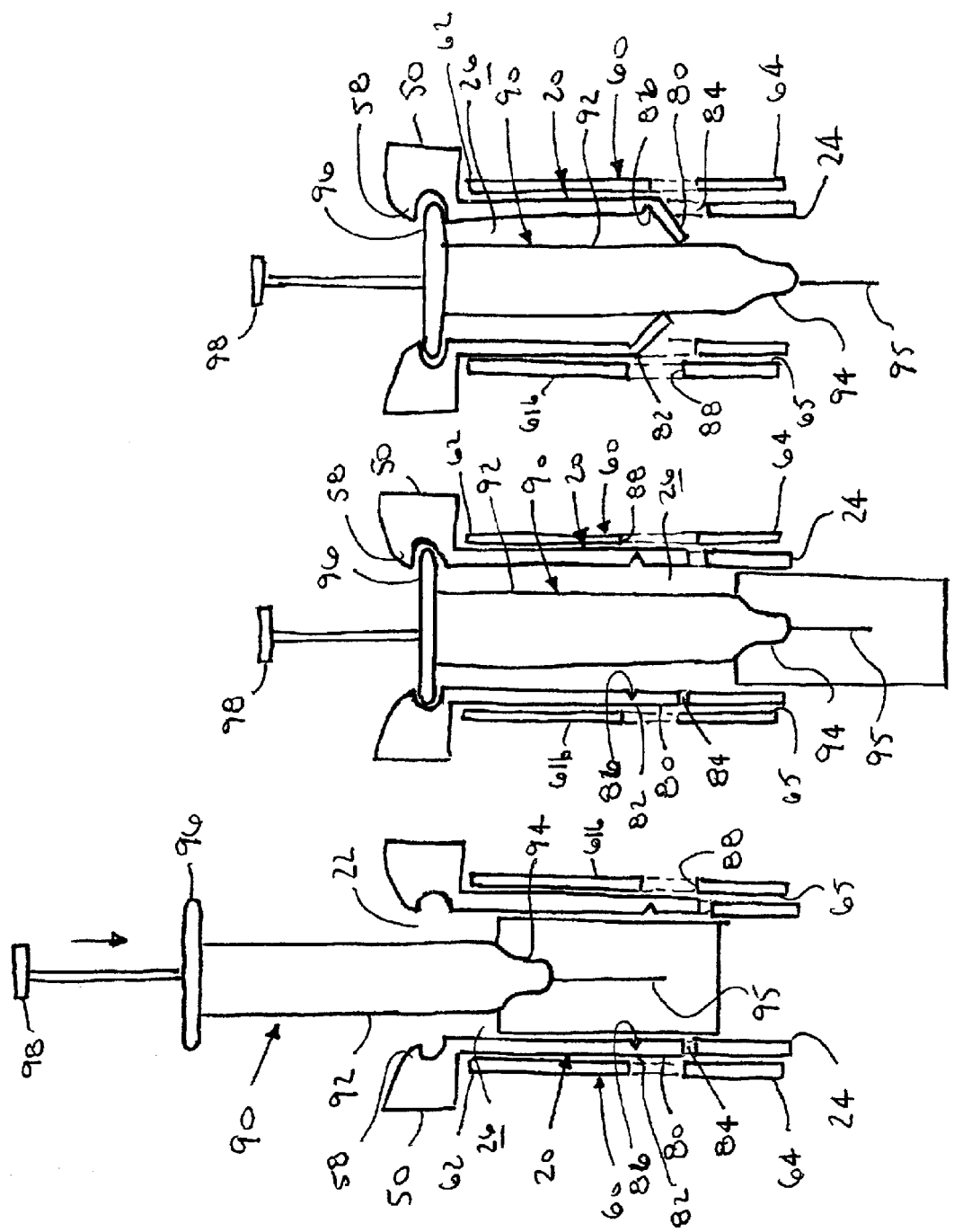

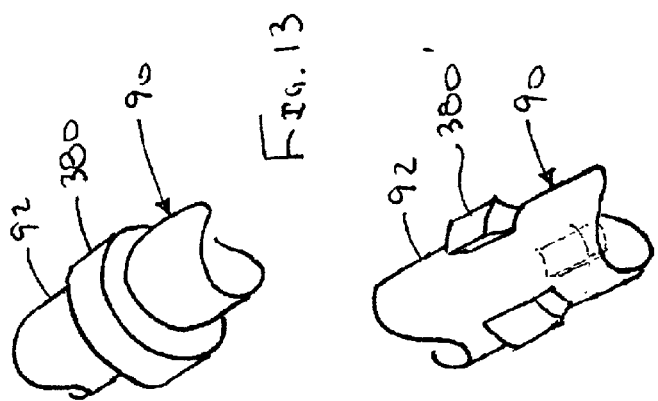
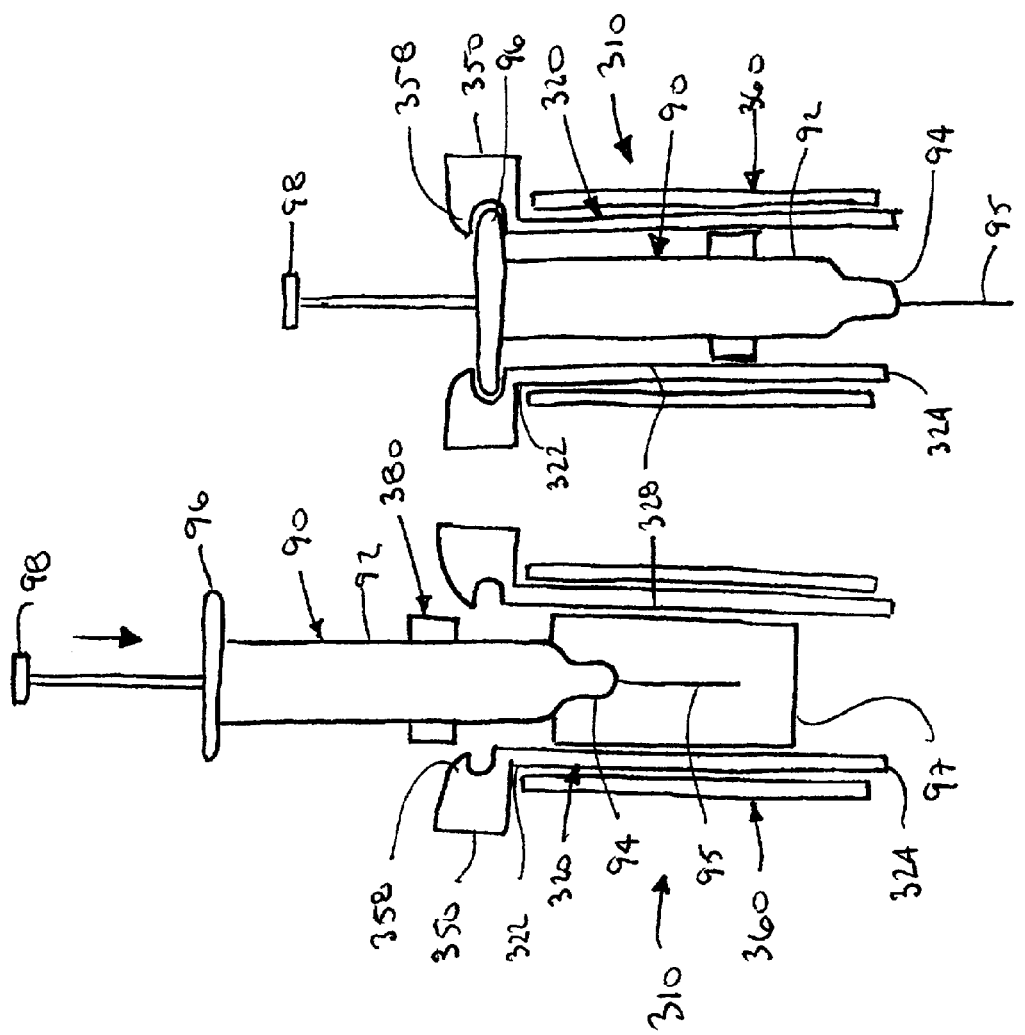

DISPOSABLE SELF-SHIELDING SYRINGE GUARD

FIELD OF THE INVENTION

The present invention relates to adapters for syringes or other medical cartridges, and more particularly to a guard for a syringe or other medical cartridge, such as a unit dose pre-filled syringe, that is used to inject medication into a patient.

BACKGROUND OF THE INVENTION

Medication is often dispensed using a unit dose medical cartridge, such as an ampoule, vial, or syringe, and a syringe holder, injector, or adapter. The cartridge typically has a barrel with a needle at one end and a plunger at the other end. Such cartridges are often referred to as "pre-filled syringes" because they contain a specific dosage or volume of medication when they are initially provided, as compared to conventional syringes, which are furnished empty and filled by the user prior to use. Alternatively, the medical cartridge may include a rubber stopper instead of a needle, and/or a piston rather than a plunger.

Because of the threat of communicable diseases, a number of syringes and adapters have been developed to prevent accidental needle sticks or inadvertent reuse of needle devices. Many of these, however, are not easy to use or are complicated to manufacture, resulting in less effective disposable syringe devices. For example, U.S. Pat. No. 5,569,211 discloses a syringe that allows the needle of the syringe to be withdrawn into the barrel of the syringe after medication is dispensed from it. This device, however, is a specially designed substitute for a conventional syringe, and cannot be used to hold commercially available pre-filled syringes.

U.S. Pat. No. 5,522,812 discloses a syringe shield device for holding a conventional cartridge not having its own needle. The device includes a cylindrical body, a double needle assembly, a cylindrical shield, a special collar piece allowing the shield to be drawn over the needle and locked, and a plunger assembly, resulting in a device that is potentially difficult and expensive to manufacture. The device also requires two hands to operate, one to hold the body, and one to rotate the shield into the locked position, which may be inconvenient to the medical professional using the device.

Another consideration with unit dose cartridges and pre-filled syringes is that they are often made from glass, particularly for holding certain vaccines or biotech drugs where concern about micro-organisms or other contaminants is most critical. Glass cartridges and pre-filled syringes are very fragile and often break during transportation or use. Some existing adapters may not adequately protect the syringe contained therein from such risks. Others provide greater protection for the cartridge, but may obstruct viewing the syringe when the device is being used, hampering monitoring the medication being delivered.

Accordingly, adapters or guards for receiving syringes or other medical cartridges would be considered useful.

SUMMARY OF THE INVENTION

The present invention is directed to adapters for syringes or other medical cartridges, and more particularly to a needle guard for a syringe or medical cartridge, such as a unit dose pre-filled syringe, that is used to inject medication into a patient.

In accordance with one aspect, the present invention provides a guard for a syringe that includes a needle, a needle protector cap, and a barrel. Generally, the guard includes a body including a cavity for receiving the syringe therein, the body having an open proximal end communicating with the cavity, and a distal end having an opening through which the needle and needle protector cap on the syringe may extend when the syringe is received in the cavity. Optionally, the body may include a locking mechanism on its proximal end for engaging the proximal end of the syringe received therein, e.g., to substantially permanently encapsulate the syringe in the body.

A shield may be slidably attached to the body that has proximal and distal ends, the distal end having an opening through which the needle and needle protector cap may extend when the shield is in an unguarded position. The shield may be slidable between the unguarded position wherein the needle is exposed and a guarded position wherein the needle is covered by the shield. One or more detents may be provided on the shield and/or body for locking the shield in the guarded position and/or unguarded position.

One or more tabs may be provided in a wall of the body and/or the shield that are deflectable from a first position wherein the tab(s) may extend along the wall or radially outwardly from the wall, to a second position wherein the tab(s) may be directed inwardly into the cavity to contact the barrel of the syringe. In one embodiment, each tab may be connected to a wall of the body, e.g., by a hinged region that may include a weakened region about which the tab may be bent inwardly towards the second position. In another embodiment, each tab may be connected to a wall of the shield and may be deflected inwardly through a slot or other opening in the body. Alternatively, a portion of the body itself may be deformed inwardly, e.g., by heating the portion until softened to allow the portion to be directed inwardly.

The guard may be configured for receiving relatively small cartridges, for example, a 0.5 mL unit dose pre-filled syringe with a rigid needle protector cap having a diameter larger than a barrel of the syringe. Once the syringe is received in the cavity, the tabs may be deflected inwardly to contact the barrel of the syringe, thereby providing lateral support for the syringe.

In accordance with another aspect, the present invention provides an injection device, including a syringe, a body, and a shield. The syringe may include a barrel, a needle extending from a distal end of the barrel, and a needle protector cap detachably covering the needle. A radial element may extend from the barrel, e.g., a "C" shaped or other substantially annular collar, or a plurality of radial tabs. The body may include a cavity extending axially between open proximal and distal ends thereof that has a cross-section for receiving the needle protector cap therethrough as the syringe is inserted into the cavity. The radial element may slidably abut or contact an inside surface of the body for preventing substantial lateral movement of the syringe within the cavity. The distal end of the body may have an opening through which the needle and needle protector cap at least partially extend when the syringe is received in the cavity.

The shield may be slidably attached to the body. A distal end of the shield may include an opening through which the needle and the needle protector cap may extend when the shield is in an unguarded position. The shield may be slidable between the unguarded position and a guarded position wherein the needle is covered by the shield. The shield and/or the body may include one or more detents for locking the shield in the guarded position and/or for holding the shield in the unguarded position.

In accordance with yet another aspect of the present invention, a method is provided for assembling an injection device. A body may be provided including open proximal and distal ends and a cavity extending therebetween. A syringe may be inserted into the proximal end of the body and into the cavity until a needle and needle protector cap on the syringe extend through the open proximal end of the body.

A portion of the body, e.g., one or more tabs on the body, may be deflected inwardly to contact the barrel of the syringe. For example, the tabs may be heated to soften a material of the tabs, and then the tabs may be deflected inwardly. In addition or alternatively, the tabs may be plastically deformed to deflect the tabs inwardly into the cavity, e.g., about a hinged region.

A locking mechanism on the body may engage the syringe to substantially permanently encapsulate the syringe within the body. A shield may be slidably attached to the body either before or after inserting the syringe into the cavity.

The injection device may then be used to deliver medication in the syringe to a patient. The needle protector cap may be removed to expose the needle on the syringe, and the needle may be injected into a patient to deliver the medication. Because the tabs contact the barrel of the syringe, the syringe may be supported from lateral movement within the cavity. After use, the shield may be advanced over the needle to a guarded position and locked in the guarded position.

In accordance with still another aspect of the present invention, a method is provided for assembling an injection device. A guard may be provided including open proximal and distal ends and a cavity extending therebetween. A syringe may be inserted into the proximal end of the guard and into the cavity until a needle and needle protector cap on the syringe extend through the open proximal end of the guard.

A portion of the guard, e.g., one or more tabs thereon, may be deflected inwardly to contact the barrel of the syringe. For example, the tabs may be heated to soften a material of the tabs, and then the tabs may be deflected inwardly. In addition or alternatively, the tabs may be plastically deformed to deflect the tabs inwardly into the cavity, e.g., about a hinged region. A locking mechanism on the guard may engage the syringe to substantially permanently encapsulate the syringe within the guard.

The injection device may then be used to deliver medication in the syringe to a patient. The needle protector cap may be removed to expose the needle on the syringe, and the needle may be injected into a patient to deliver the medication. Because the tabs contact the barrel of the syringe, the syringe may be supported from lateral movement within the cavity. After use, a shield on the guard may be advanced over the needle to a guarded position and locked in the guarded position to prevent reuse and/or substantially reduce the risk of accidental needle sticks.

Other features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which:

FIGS. 6A–C are cross-sectional side views of the syringe guard of FIGS. 5A and 5B, showing a syringe being received therein.

FIGS. 12A and 12B are cross-sectional side views of another embodiment of a syringe guard, receiving a syringe therein.

FIG. 13 is a perspective detail of a syringe barrel with an annular collar thereon.

FIG. 14 is a perspective detail of a syringe barrel with a plurality of radial tabs thereon.

DETAILED DESCRIPTION OF THE INVENTION

Figure 1:
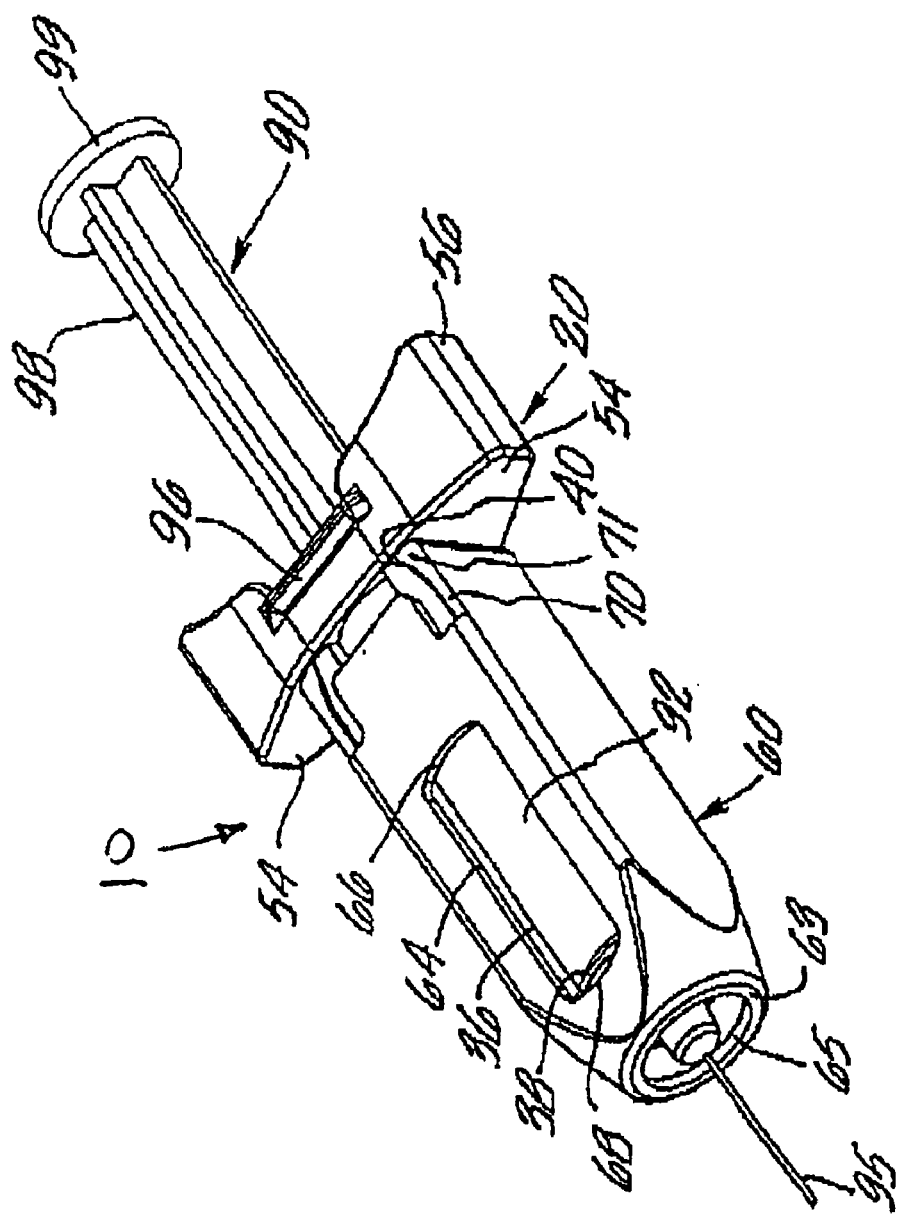
FIG. 1 is a perspective view of a first preferred embodiment of a syringe guard of the present invention, holding a syringe.

Turning to the drawings, FIGS. 1–7B show a first preferred embodiment of a syringe guard 10 for holding a syringe 90. Generally, the guard 10 includes a housing or body 20 for receiving and holding the syringe 90, and a protective case or shield 60 slidably attached to the body 20. Both the body 20 and the shield 60 are generally molded from plastic, such as polypropylene, synthetic resinous polymers of butadiene and styrene, or polycarbonate, and are preferably clear and substantially colorless to facilitate observation of the syringe received therein. Alternatively, they may be translucent or opaque, and may be colored, such as a latex color, or a flesh tone, such as off-white, brown, or black.

Turning to FIGS. 2A–2C and 6A–6C, the body 20 is an elongate tubular member, preferably having a substantially rectangular cross-section, including two side rails 28, an open proximal end 22, and an open distal end 24. The rectangular shape may be preferred as it may enhance rigidity and/or protect the syringe 90 (not shown) therein from lateral forces that may otherwise damage it, particularly if the syringe 90 is made of glass. Alternatively, instead of the rectangular cross-section, the body 20 (and shield 60) may have corresponding oval or round cross-sections (not shown) providing sufficient rigidity to protect the syringe 90 received therein. In addition, the body 20 may have a substantially rigid collar 32 on the distal end 24, and a finger grip 50 on the proximal end 22, both attached to or preferably integrally molded onto the body 20. Alternatively, instead of including opposing side rails 28, the body 20 may include a substantially rectangular body including four side walls (not shown).

The two side rails 28 generally have a "C" shape and define a cavity 26 in the body 20, the cavity 26 extending axially from the proximal end 22 to the distal end 24 of the body 20. The inside surface 30 of the rails 28 may be flat or concave, e.g., conforming substantially to the outer diameter of a standard syringe (not shown). Optionally, if the side rails 28 have a flat or "C" channel inside surface 30, guide rails (not shown, see FIGS. 7A-7D) or the like may be provided on the inside surface 30 to direct the syringe 90 into the cavity 26, as described further below.

The body 20 includes tabs 80 in each side rail 28 (or in one or more side walls). The tabs 80 may be defined by generally "C" shaped slots 84 in side rails 28 (best seen in FIG. 2A) that are connected to the side rails 28 by hinged regions 82 (shown in FIGS. 6A-6C). The tabs 80 may extend axially along the side rails 28, e.g., towards the distal end 24 of the body 20 (see FIG. 10B) or towards the proximal end 22 of the body 20 (not shown). Alternatively, tabs (not shown) may be provided in the shield 60, and the body 20 may include corresponding slots (not shown) in the side rails 28, as described further below.

The tabs 80 are deflectable from an initial position, e.g., extending axially (shown in FIGS. 2A and 6A) or radially outwardly (not shown), to a second position (shown in FIG. 6C) such that the tabs 80 extend inwardly into the cavity 26 for engaging a barrel 92 of a syringe 90 received in the body 20, as described further below. The hinged regions 82 may include living hinges 82 formed from a material that may be softened upon heating to allow the tabs 80 to be deflected inwardly. In addition or alternatively, the hinged regions 82 may include weakened regions 86 (shown in FIGS. 6A-6C), e.g., such that the tabs 80 may be plastically deformed inwardly, i.e., substantially irreversibly deflected, to contact the barrel 92.

Figure 3:
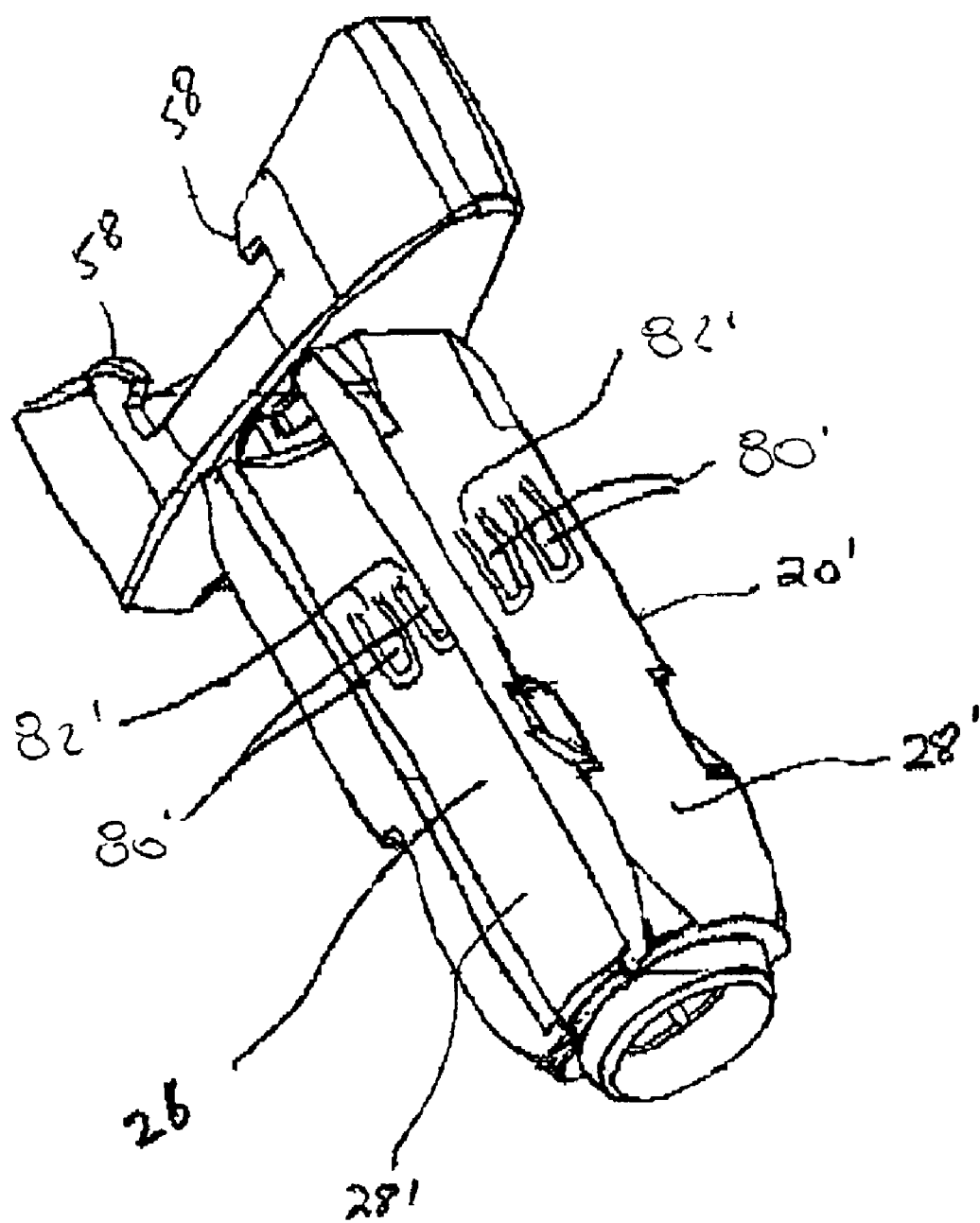
FIG. 3 is a perspective view of an alternative embodiment of a body for the syringe guard of FIG. 1.

Although a single tab 80 is shown in each side rail 28, in an alternative embodiment, the body 20' may include a plurality of tabs 80' in one or more side rails 28,' as shown in FIG. 3. Multiple tabs 80' may enhance lateral support of the barrel 92 of the syringe 90, as compared to a single tab 80. The tabs 80' may be provided adjacent one another across a width of the side rail 28' and/or may be provided axially from one another (not shown).

Returning to FIGS. 2A and 2C, the finger grip 50 generally includes a pair of wing-like members 52 molded onto the proximal end 22 of the body 20, thereby generally defining a "T" shape. Each wing-like member 52 includes a distal surface or finger ledge 54, and an outer gripping surface 56 extending proximally from the outer edge 54a of the finger ledge 54. The outer gripping surface 56 may include a lip, grooves or other irregularities (not shown) protruding radially from its proximal end or set in the surface 56, if desired to improve the hold on the finger grip 50. Lateral surfaces 55 extend proximally from the finger ledges 54 between the gripping surfaces 56, thereby defining a recess or open proximal end 51 communicating with the cavity 26 in the body 20.

The finger grip 50 may include a locking mechanism for securing a syringe 90 in the body 20. For example, the lateral surfaces 55 of the finger grip 50 may include a plurality of locking detents 58 partially defining an aperture or slot 57 for holding the syringe 90 inserted into the cavity 26, as described further below. Alternative embodiments of locking mechanisms that may be provided in the finger grip 50 are shown in U.S. Pat. No. 6,159,184, the disclosure of which is expressly incorporated herein by reference.

Figure 2A:
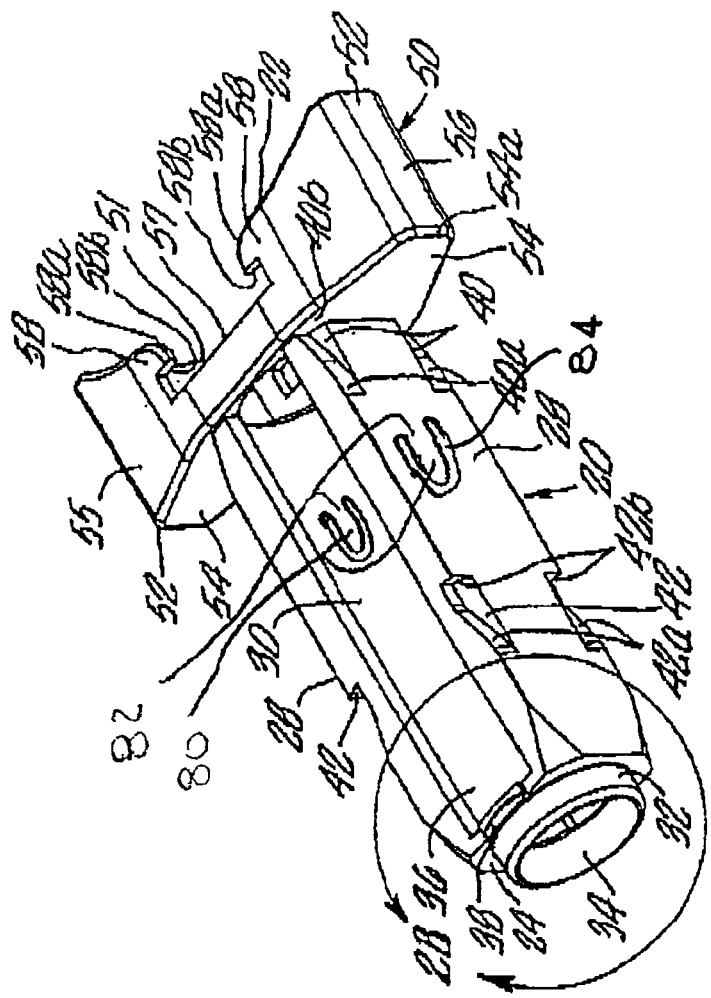
FIGS. 2A, 2B and 2C are perspective views of a body of the syringe guard of FIG. 1.
Figure 2B:
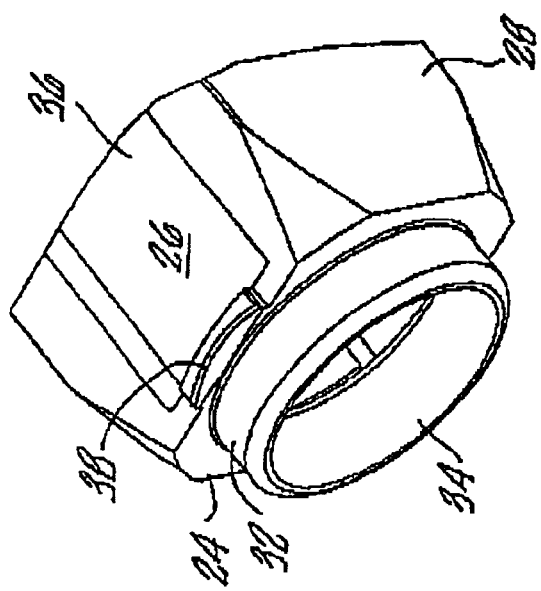

Turning to FIG. 2B, the collar 32 on the distal end 24 preferably has a substantially annular shape, including an opening 34 extending therethrough to allow the needle and needle cover on the pre-filled syringe (not shown) in the cavity 26 to extend beyond the body 20. The opening 34 may have a diameter smaller than the cavity 26 such that the distal end 24 may retain the syringe 26 inside the cavity 26, e.g., preventing distal movement in addition to or instead of the locking mechanism in the finger grip 50. Alternatively, the distal end 24 may be tapered or otherwise partially obstructed such that it engages a distal end 94 of the syringe 90, e.g., preventing distal movement of the syringe 90, while allowing a needle 95 and needle cover (not shown) to extend beyond the distal end 24.

Alternatively, the distal end 24 may include an expandable "collet" (not shown) defined by a plurality of longitudinal slots extending proximally a short distance from the distal end 24. The collet may have a diameter smaller than that of the syringe barrel, hub or needle cap as desired, thereby allowing the distal end 24 to be resiliently expanded to substantially engage the syringe received therein. In a further alternative, the opening 34 in the distal end 24 may have a sufficiently large diameter to freely allow the distal end 94 of the syringe 90 to extend therethrough, the syringe 90 being locked substantially within the body 20 exclusively by a locking mechanism on the proximal end 22 or finger grip 50 of the body 20.

Returning to FIG. 2A, elongate openings or windows 36 may be provided in the side rails 28, e.g., extending longitudinally between the finger grip 50 and the distal end 24, and allowing observation of the syringe 90 held in the body 20. Alternatively, if a four-walled body is provided, an elongate opening or window may be integrally formed in one or more of the side walls, preferably in two walls on opposite sides of the body 20. The body 20 may also include one or more stop tabs 38 attached or molded directly to the body 20. Preferably, stop tabs 38 are molded onto the body 20 on two opposite sides of the distal end 24 of the body 20. Additional information on stop tabs 38 that may be included on the body 20 may be found in U.S. Pat. No. 6,030,366, the disclosure of which is expressly incorporated herein by reference.

The body 20 may also include one or more sets of detents, preferably having a set of proximal detent pockets 40 adjacent the finger grip 50, and a set of distal detent pockets 42 at a more distal location on the body 20. The detent pockets 40, 42 may lock the relative movement between the shield 60 and body 20, as explained more fully below.

Figure 4A:
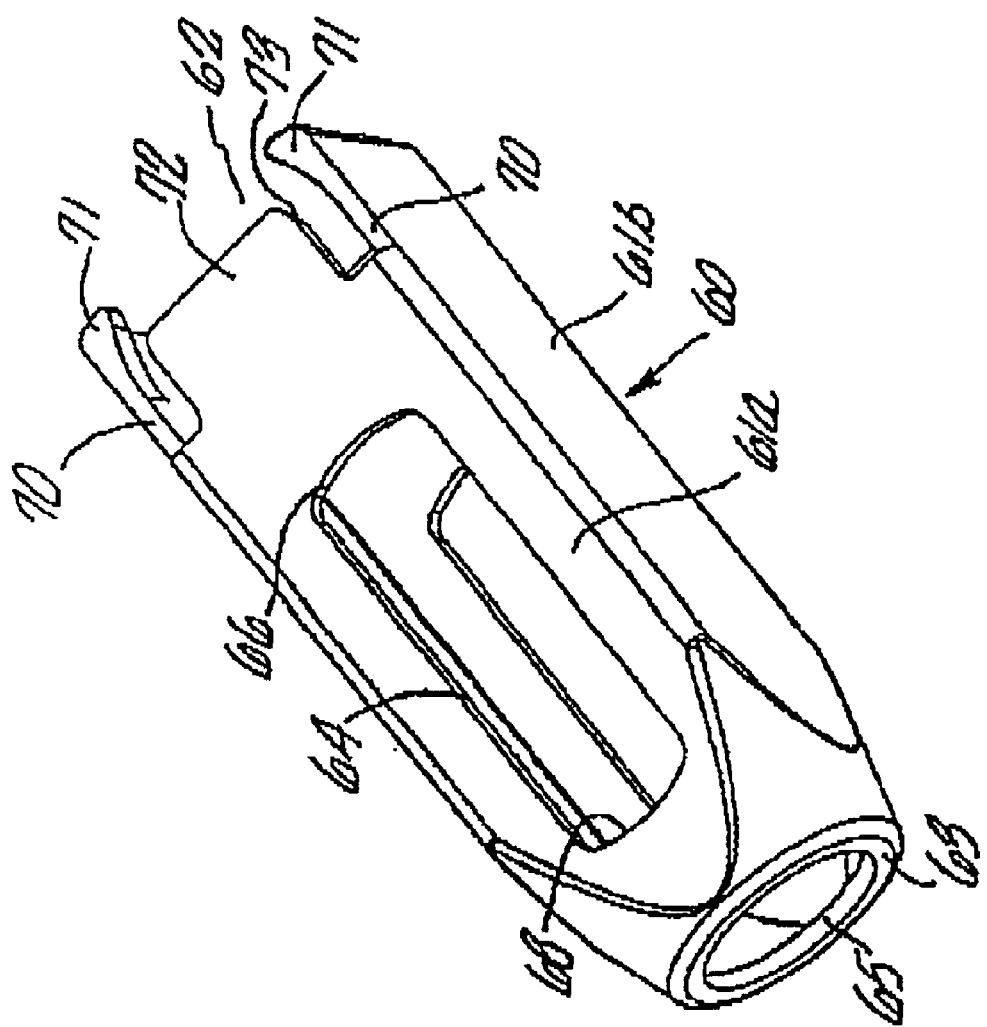
FIGS. 4A and 4B are perspective views of a shield of the syringe guard of FIG. 1.
Figure 4B:
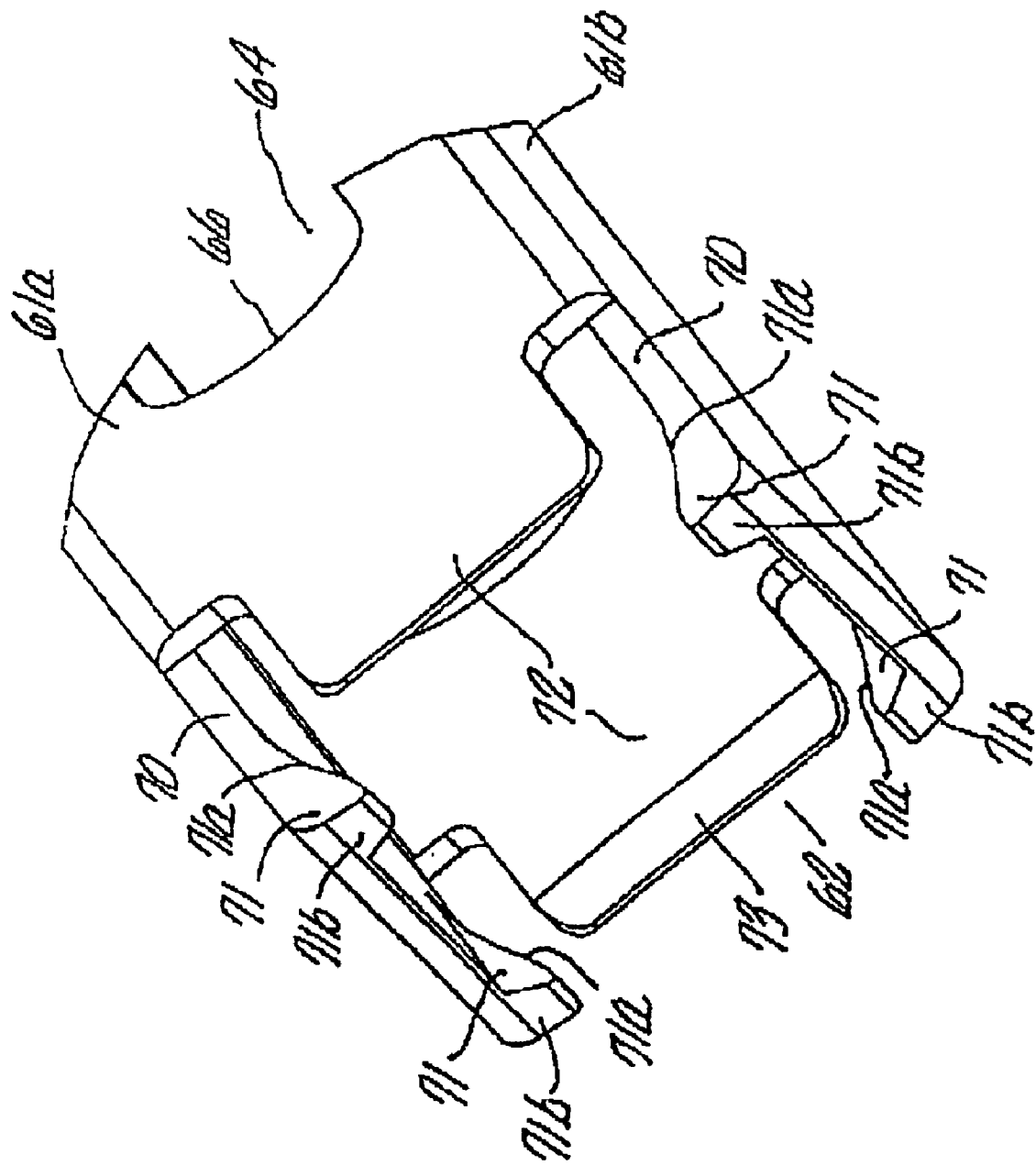

Turning to FIGS. 4A and 4B, the protective case or shield 60 may be a tubular member adapted to slidably fit on the body 20, preferably having a substantially rectangular interior shape that conforms to the shape of the body 20. The shield 60 may include four side walls 61a, 61b, an open proximal end 62, and an open distal end 63. The shield 60 may have a pair of detent arms 70 and a plurality of detents 71 attached to or preferably integrally molded directly into the side walls 61b. Assembly tabs 72 with sloping or ramped interior surfaces 73 may also be molded into and extend proximally from the side walls 61a.

The detents 71 preferably have shapes corresponding substantially to the shapes of the detent pockets 40, 42 in the body 20 (not shown, see FIG. 2A). The proximal edges 71b are blunt or preferably oblique to engage the proximal surfaces 40b or 42b of the detent pockets 40, 42 in the body 20, as described further below. For example, the detents 71 and detent pockets 40, 42 may have complementary shapes to cooperate in order to maximize bearing surface area, particularly to stabilize a shorter guard 10. In addition, the detent arms 70 may vary in size and thickness in embodiments adapted to accommodate a variety of syringes. Additional information on cooperating detents for use with the present invention may be found in U.S. Pat. Nos. 6,030,366 and 6,159,184, the disclosures of which are incorporated by reference above.

At least one wall 61a, and preferably the two opposite walls 61a, may include an elongate opening or window 64 therethrough. The window(s) 64 may allow observation of the syringe 90 received in the body 20, and/or may provide a traveling slot for the stop tab(s) 38 (not shown, see FIG. 2B) on the body 20. The window 64 has a proximal edge 66 and a distal edge 68 defined by the wall 61a that limit the relative movement of the shield 60 to the body 20, as explained more fully below. Alternatively, the window 64 may be divided by a cross-member (not shown) molded into the wall 61a that extends transversely across the window 64 if it is desired to further limit the movement of the shield 60. Optionally, the side walls 61a, 61b may include wings, a ring, or other finger holds (not shown) extending radially from the shield 60 to ease movement of the shield 60 relative to the body 20. In addition, the side walls 61a, 61b may provide a flat surface onto which a label may be applied, for example, to identify the drug or other fluid contained within the syringe 90 received within the guard 10, or an embossed pattern may be molded, possibly including a name or a logo.

Figure 5A:
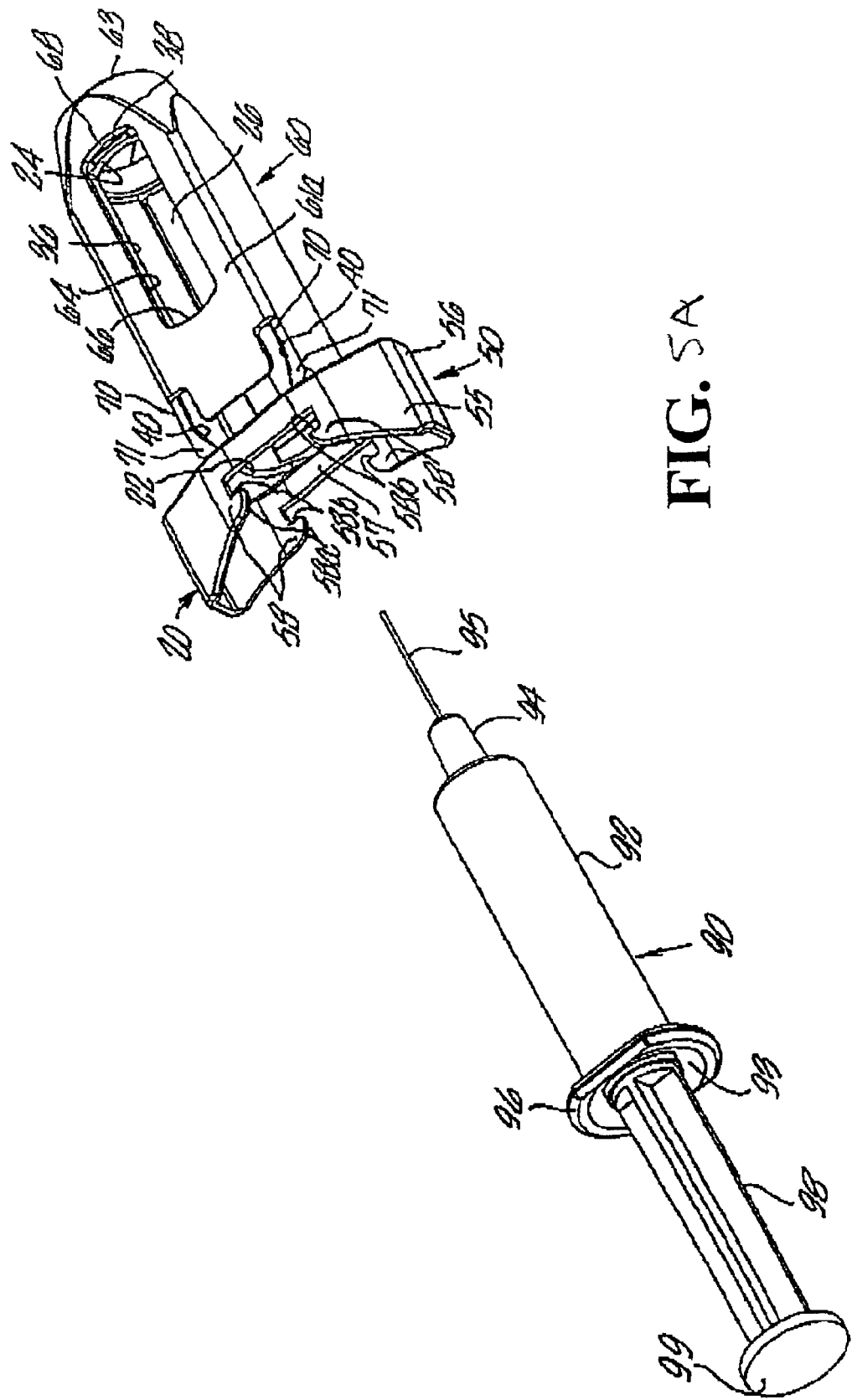
FIGS. 5A and 5B are perspective views of the syringe guard of FIG. 1 receiving a syringe therein.
Figure 5B:
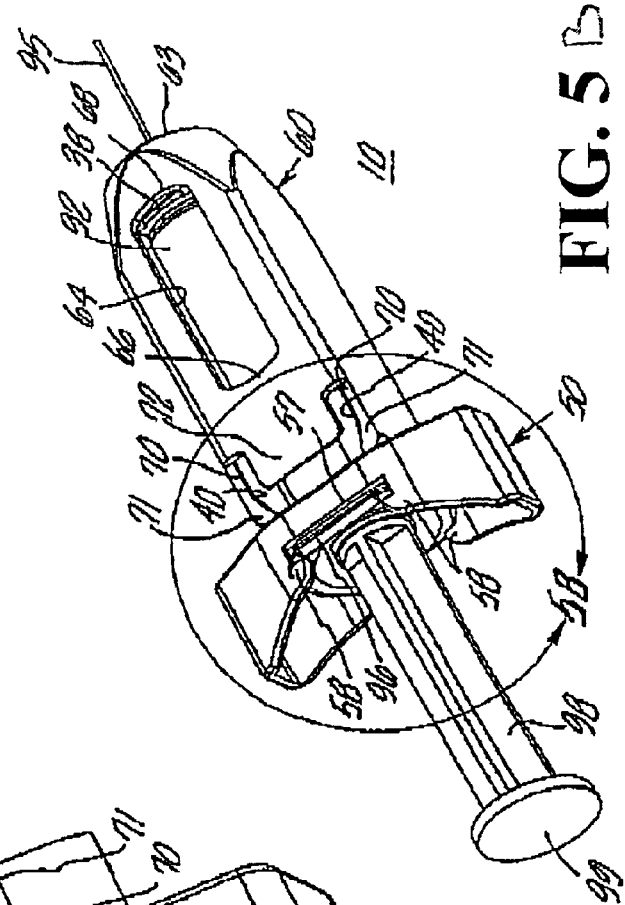

Turning to FIGS. 5A and 5B, the guard 10 is normally provided with the body 20 and shield 60 pre-assembled as shown. To assemble the guard 10, the distal end 24 of the body 20 (FIG. 2A) may be inserted into the open proximal end 62 (FIG. 4A) of the shield 60, with the window 36 in the body 20 aligned with the side wall 61a of the shield 60 having the window 64 therein. As the body 20 is inserted, the stop tab(s) 38 may engage the tapered interior edge(s) 73 of the assembly tab(s) 72 on the shield 60 (FIG. 4B), allowing the stop tab(s) 38 to pass under the wall(s) 61a. After each stop tab 38 passes under the respective wall 61a, the stop tab 38 may then enter the window 64 and travel freely therein.

Figure 7A:
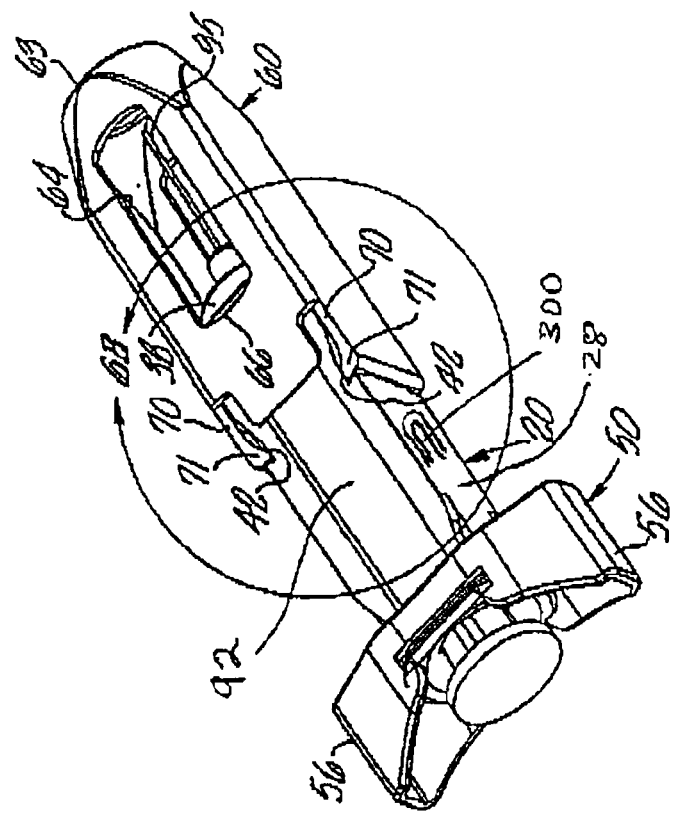
FIG. 7A is a perspective view of the syringe guard of FIGS. 5A and 5B, with the shield locked in a guarded position.
Figure 7B:
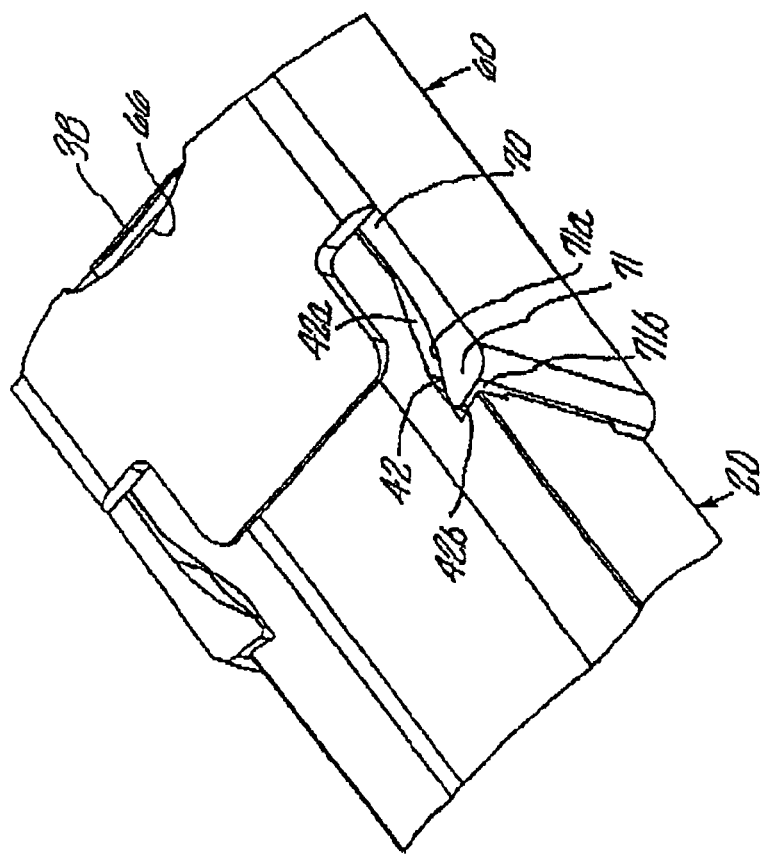
FIG. 7B is a perspective view of the syringe guard of FIG. 7A, showing cooperating detents locking the shield in the guarded position.
Figure 8B:
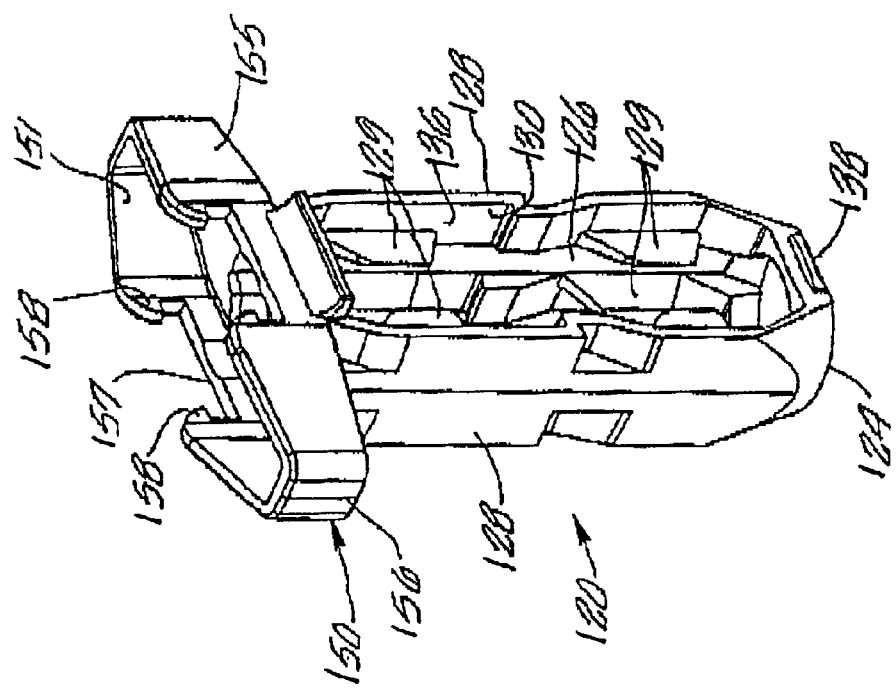
FIGS. 8A and 8B are perspective views of an alternative embodiment of a body for a syringe guard.
Figure 8A:
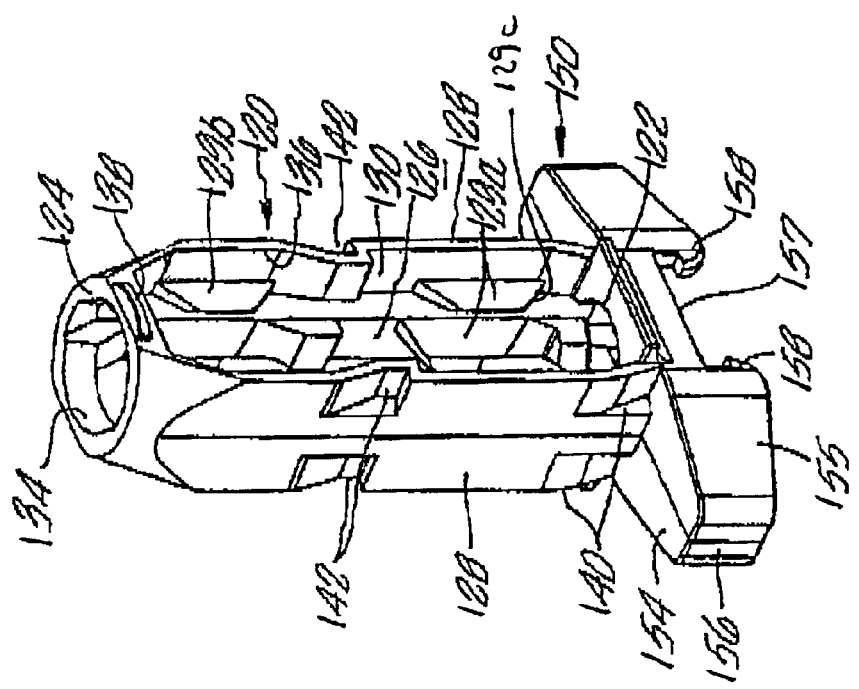

Together, the stop tab(s) 38 and window(s) 64 may allow the shield 60 to slidably move in relation to the body 20, but may substantially define the limits of that relative movement. The shield 60 may slide proximally and distally until each stop tab 38 abuts a distal edge 68 and a proximal edge 66, respectively, of the respective window 64. Specifically, when the stop tab 38 engages the distal edge 68 of the window 64, as shown in FIG. 5A, the shield 60 is in a proximal or unguarded position. When the stop tab 38 engages the proximal edge 66 of the window 64, as shown in FIGS. 7A and 7B, the shield 60 is in a distal or guarded position.

Referring to FIGS. 5A and 5B, when the stop tab 38 abuts the distal edge 68 of the window 64, the detents 71 and proximal detent pockets 40 operate to hold the shield 60 in the unguarded position. The sloping distal edges 71a of the detents 71 engage the sloping distal edges 40a of the proximal detent pockets 40 on the body 20, thereby preventing the shield 60 from moving distally. In the unguarded position, the shield 60 may include one or more openings 88 (not shown, see FIGS. 6A–6C) in the walls 61 that overlie the tabs 80 (FIG. 2A) in the side rails 28 of the body 20.

Returning to FIGS. 5A–6C, once assembled, the guard 10 is ready to receive a cartridge, such as a conventional unit dose pre-filled syringe 90. Although a pre-filled syringe 90 is the preferred delivery device that may be used with the guard 10, the guard 10 may be used for other pre-filled or unit dose delivery systems and/or conventional hypodermic syringes, and the term syringe and cartridge includes other such known systems. The syringe 90 generally has a substantially smooth-walled cylindrical barrel 92, a distal end or hub 94 including a hypodermic needle 95, a needle cover or cap (not shown), an enlarged proximal end 93 having a flange 96, and a plunger 98. The flange 96 may have a sufficiently large width to provide a finger grip for the syringe 90, or may simply be a small lip to facilitate manufacturing, for example, on a filling line.

Preferably, the syringe 90 includes a rigid nose shield or needle protector cap 97 (shown in FIGS. 6A and 6B) having a diameter larger than the diameter of the barrel 92 of the syringe 90. For example, the syringe 90 may be a conventional 0.5 ml capacity pre-filled syringe.

The distal end 94 of the syringe 90 may be inserted into the recess 51 of the finger grip 50 and the open proximal end 22 of the body 20. The syringe 90 may enter the cavity 26 and progress distally until the distal end 94 of the syringe 90 becomes coextensive with and/or extends beyond the distal end 24 of the body 20. The cross-section of the cavity 26 is sufficiently large to accommodate the needle protector cap 97 passing through the cavity 26 and at least partially through the opening 34 in the distal end of the body 20. A needle protector cap 97 of the syringe 90 may partially enter the opening 34 and engage the collar 32, thereby providing protection from lateral movement of the syringe 90.

Figure 2C:
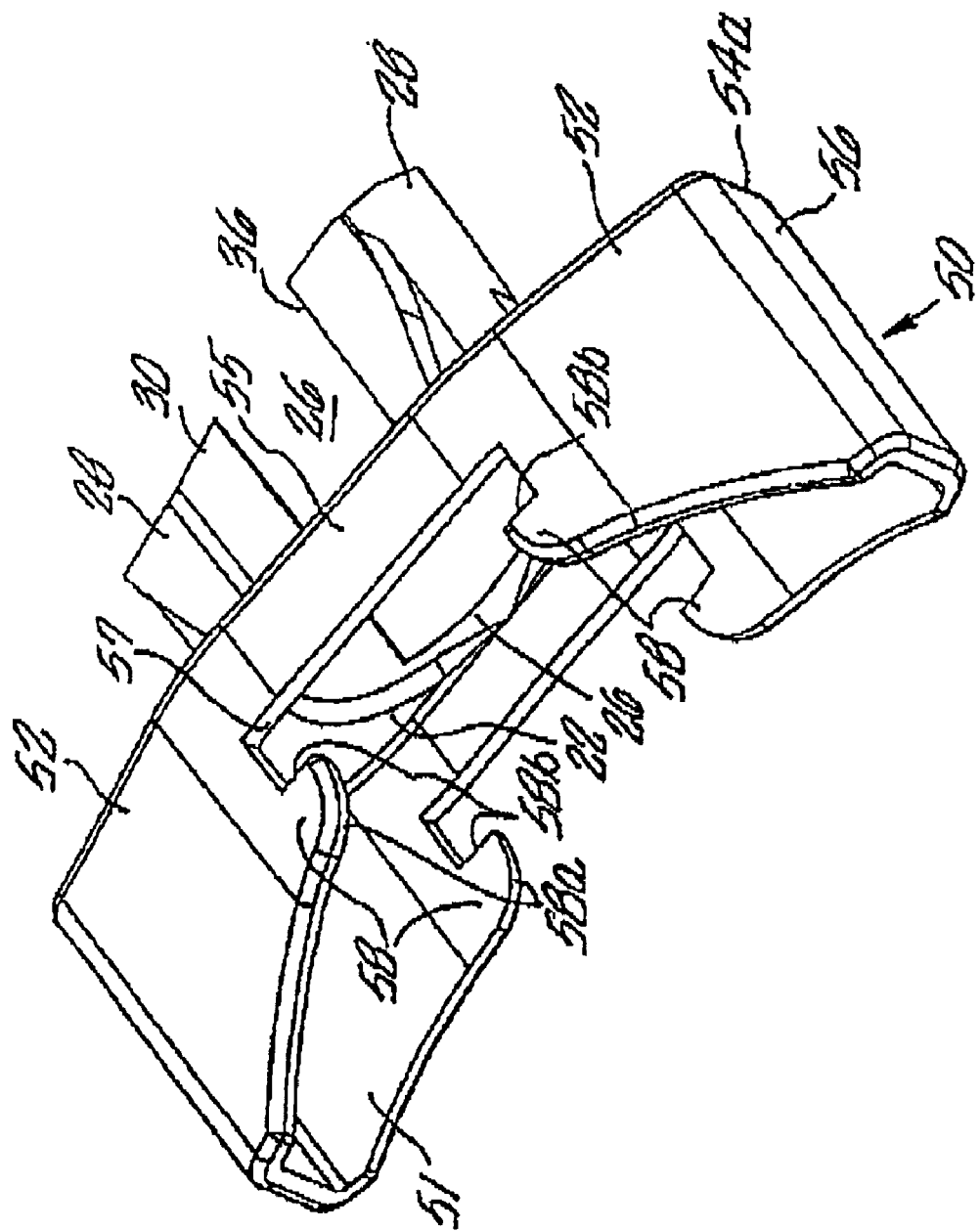
Figure 5C:
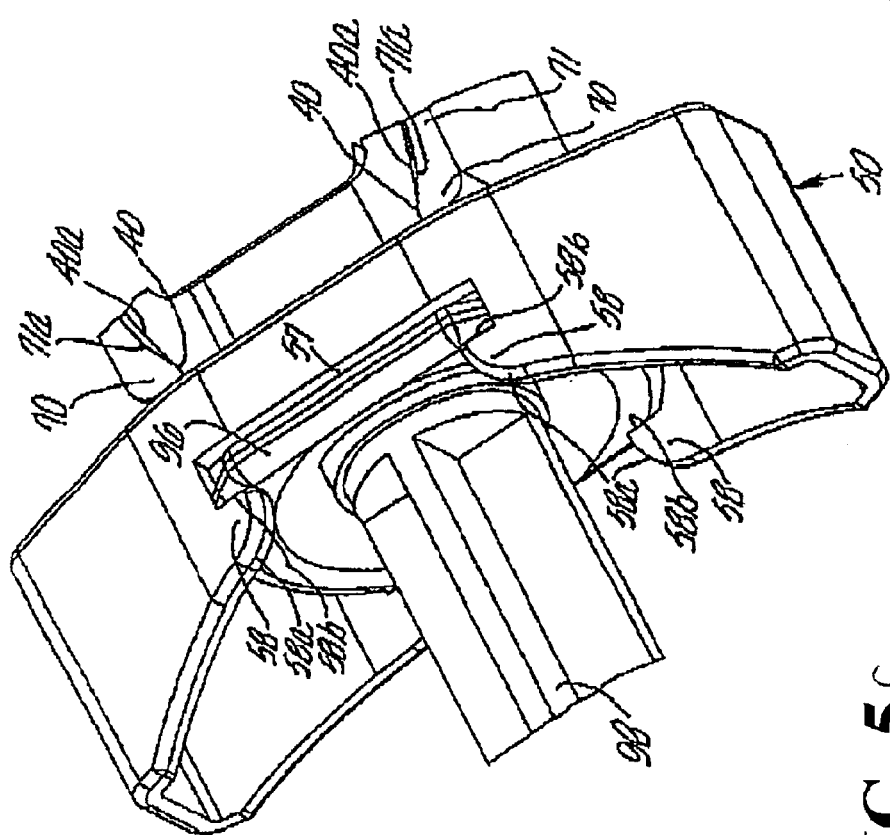
FIG. 5C is a detail of a proximal end of the syringe guard of FIG. 5B, showing a locking mechanism for securing the syringe in the syringe guard.

As the syringe 90 becomes fully encapsulated within the cavity 26, the flange 96 on the proximal end 93 of the syringe 90 may contact the locking detents 58 on the finger grip 50. The locking detents 58 may have tapered proximal edges 58a, allowing the syringe 90 to be directed further distally, the flange 96 moving the locking detents 58 aside and entering the slot 57. As best seen in FIGS. 2C and 5C, the locking detents 58 preferably have blunt distal edges 58b, which prevent the syringe 90 from being removed proximally from the slot 57, thereby substantially permanently locking the syringe 90 into the body 20. Thus, the slots 57 preferably substantially permanently lock the proximal end 93 of the syringe 90 within the finger grip 50, thereby preventing axial (i.e., proximal and/or distal) movement of the syringe 90 within the guard 10. Additional information on inserting the syringe 90 into the guard 10 may be found in U.S. Pat. No. 6,159,184, incorporated by reference above.

With particular reference to FIGS. 6B and 6C (in which the cooperating detents on the body 20 and shield 60 have been omitted for convenience), once the syringe 90 is locked into the guard 10, the needle 95 and a needle protector cap 97 may extend through the opening 34 in the collar 32 and the opening 65 in the distal end 63 of the shield 60. The length of the shield 60 may be substantially coextensive with the barrel 92 of the syringe 90, allowing the full length of the needle 95 to extend beyond the distal end 63 of the shield 60, but protecting the hub 94 of the syringe 90.

Referring particularly to FIG. 6C, the tabs 80 (FIG. 2A) in the side rails 28 of the body 20 may be deflected inwardly to substantially abut or otherwise contact the barrel 92 of the syringe 90. For example, the hinged regions 82 may be plastically deformed, thereby bending the tabs 80 inwardly. Alternatively, heat may be applied to the tabs 80, e.g., along the hinged regions 82, in order to soften the material and allow the tabs 80 to be deformed inwardly. The shield 60 may include openings 88 in its side walls 61b, e.g., for inserting tools, heating elements, and the like (not shown) through the openings 88 in order to contact and/or bend the tabs 80. Alternatively, the syringe 90 may be inserted into the body before attaching or retracting the shield 60 to the body 20, such that the openings 88 may be unnecessary.

The syringe 90 encapsulated within the guard 10 may then be used in a conventional manner to deliver medication contained in the barrel 92. The medical professional may hold the assembled injection device using the finger ledges 54 (see FIG. 1) and the plunger 98. The needle protector cap 97 may be removed, as shown in FIG. 6C, the needle 95 may be inserted into a patient (not shown), and the medication may be delivered by directing the plunger 98 distally with the thumb. As can be seen from FIGS. 1 and 5B, the windows 64 and 36 allow observation of the barrel 92 of the syringe 90, allowing the user to closely monitor delivery of the medication. The finger grip 50 also preferably has a sufficiently large size relative to the flange 96 to provide improved manipulation by the user as compared to using the flange 96 of the syringe 90 alone.

Because the barrel 92 of the syringe 90 is smaller than the needle protector cap 97, once the needle protector cap 97 is removed, the barrel 92 of the syringe 90 may have a tendency to move laterally within the cavity 26 during use, e.g., if the needle 95 is injected into a patient and the guard 10 is moved by the user. However, with the tabs 80 engaging the barrel 92, the barrel 92 may be laterally supported, thereby minimizing or preventing such movement and substantially stabilizing the syringe 90.

After the medication is dispensed, the needle 95 may be withdrawn from the patient, and the shield 60 may be advanced over the needle 95 to the guarded position. The user may hold the body 20, typically by placing his ring finger on the gripping surface 56 adjacent his middle finger, and moving his thumb from the plunger 98 to the other gripping surface 56. The index and middle fingers, already adjacent the side walls 61b of the shield 60, grip the walls 61b and may be moved distally, thereby sliding the shield 60 distally until it reaches the guarded position, shown in FIG. 7A. Alternatively, while one hand may hold the finger grip 50, the shield 60 may be directed to the guarded position with the free hand of the user.

Because the cooperating detents 71 and detent pockets 40 (best seen in FIG. 5C) hold the shield 60 in the unguarded position, force must be applied to move the shield 60 distally. As previously discussed, the detents 71 have sloping distal edges 71a and blunt or oblique proximal edges 71b (see FIG. 4B), and similarly, the proximal detent pockets 40 have sloping distal edges 40a (see FIG. 5C) and blunt or oblique proximal edges 40b (see FIG. 2A). Because of the sloping distal edges 71a, 40a, the engagement between the detents 70 and the proximal detent pockets 40 may be overcome by pushing the shield 60 distally in relation to the body 20. The detent arms 70 move radially outward as the detents 71 move distally up the sloping edges 40a until the detents 71 leave the detent pockets 40. The shield 60 may then be moved freely, the stop tab 38 traveling along the window 64, until the stop tab 38 abuts the proximal edge 66 of the window 64, reaching the guarded position shown in FIG. 7A.

Alternatively, the guard 10 may include an internal spring for automatically biasing the shield 60 towards the guarded position. For example, the shield 60 may be automatically activated upon completing an injection, e.g., using a guard (not shown) such as that disclosed in co-pending U.S. patent application Ser. Nos. 09/566,224 and 09/724,657, the disclosures of which are expressly incorporated herein by reference.

In a further alternative, the shield 60 may include one or more tabs (not shown) instead of or in addition to the tabs 80 in the body 20. In this alternative, the body 20 may include one or more slots or other openings (not shown) that underlie respective tabs, thereby allowing the tabs to be deflected inwardly through the openings to contact the barrel 92 of the syringe 90. The openings in the body 20 may be longitudinal slots that allow the tabs to travel along the slots as the shield 60 is directed between the unguarded and guarded positions, while continuing to laterally support the barrel 92.

Alternatively, the openings may only underlie the tabs in the unguarded position and may not extend towards the distal end 24 of the body 20. In this alternative, the tabs preferably extend proximally, i.e., generally towards the proximal end of the shield 60. As the shield 60 is advanced towards the guarded position, the tabs may advance along the openings until the openings end, whereupon the tabs may be deflected outwardly out of contact with the barrel 92, yet allow the shield 60 to be advanced completely to the guarded position.

As shown in FIGS. 7A and 7B, because of the predetermined location of the distal detent pockets 42, when the stop tab 38 reaches the proximal edge 66 of the window 64, the detents 71 may substantially simultaneously enter the distal detent pockets 42 having sloped distal edge 42a and blunt proximal edge 42b. The blunt or oblique proximal edges 71b of the detents 71 may engage the similarly shaped proximal edges 42b of the distal detent pockets 42, thereby preventing the shield 60 from being moved proximally. The corresponding shape of the engaged proximal edges 71b, 42b may also maximize bearing surface to prevent misalignment of the shield 60. Furthermore, because the stop tab 38 abuts the proximal edge 66 of the window 64, the shield 60 may not be moved further distally. Thus, the shield 60 is thereby substantially permanently locked in the guarded position.

As can be seen from FIG. 7A, when the shield 60 is moved distally into the guarded position, the distal end 63 of the shield 60 passes over the needle 95, covering the needle 95. Once the shield 60 is locked in the guarded position, the needle 95 is no longer accessible, thereby substantially eliminating the risk of accidental sticks, and preventing reuse of the syringe 90. The guard 10 and pre-filled syringe 90 may then be disposed of safely.

Turning to FIGS. 8A–9B, and 9, another embodiment of a guard 110 is shown for receiving a syringe 90 with a relatively small barrel 92. The guard 110 includes a body 120 and a shield 60, the latter being substantially similar to the embodiment described above. The body 120 generally includes a pair of rails 128 defining a cavity 126 for receiving the syringe 90, a finger grip 150 on a proximal end 122 and a distal end 124, similar to the embodiment described above. The rails 128 may have a "C" cross-section as described above, or may have a substantially flat shape as shown. In addition, inside surfaces 130 of the rails 128 may include one or more semi-rigid members or ribs 129 extending from the surfaces 130 into the cavity 126. The ribs 129 are resiliently deflectable to facilitate insertion of the syringe 90 and/or enhance a rigidity characteristic of the body 120. Preferably, the ribs 129 are provided in pairs integrally formed in the side rails 128 to at least partially define a diameter or cross-sectional space similar to the diameter of the barrel 92 of the syringe 90. Optionally, a first set of ribs 129a may be provided at or near the proximal end 122 of the body 120, and a second set of ribs 129b may be provided at or near the distal end 124. The first or proximal set of ribs 129a may act as lead-in ribs to guide the pre-filled syringe 90 during insertion. The lead-in ribs 129a may have substantially tapered proximal edges 29c to align the needle cap 97.

Figure 9A:
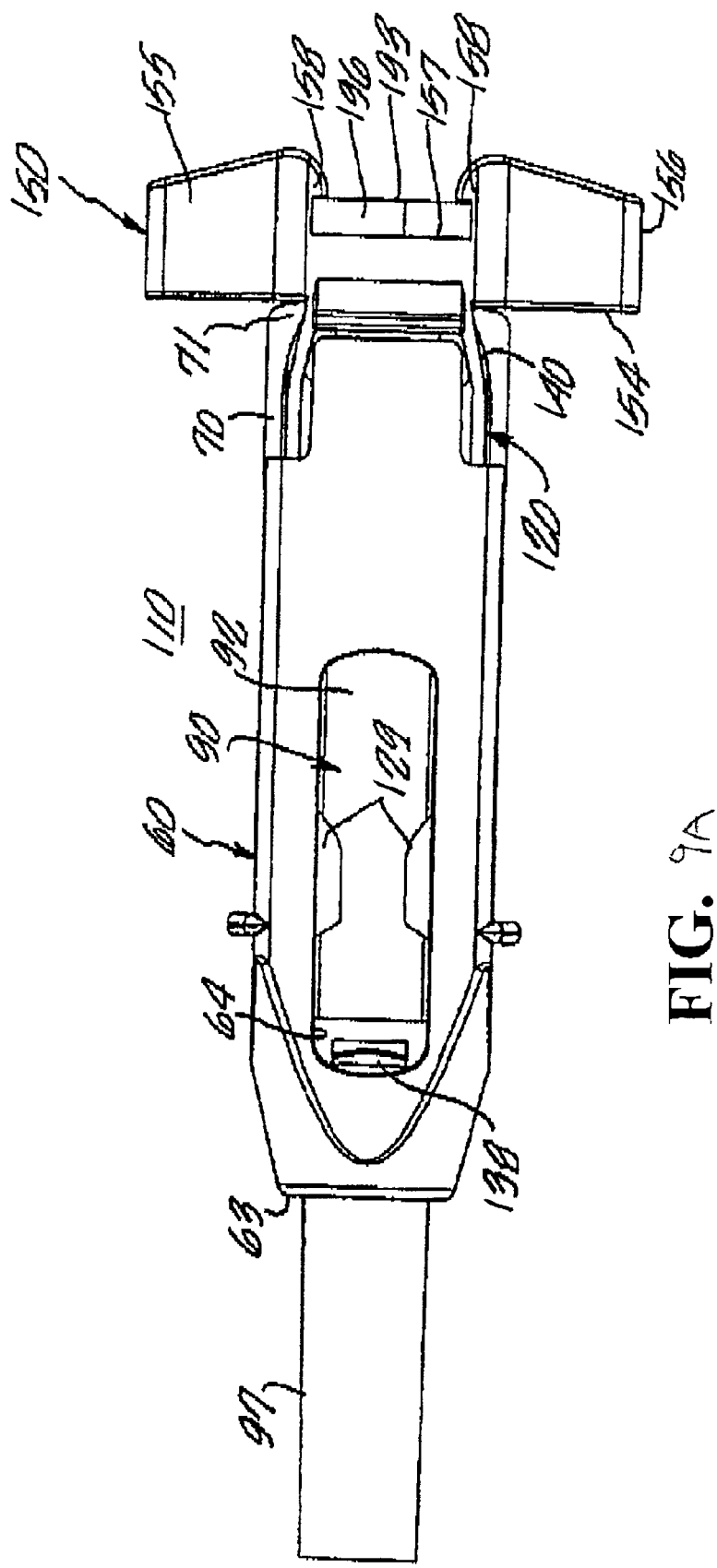
FIGS. 9A and 9B are side views of an alternative embodiment of a syringe guard including the body of FIGS. 8A and 8B, showing a shield in unguarded and guarded positions, respectively.
Figure 9B:
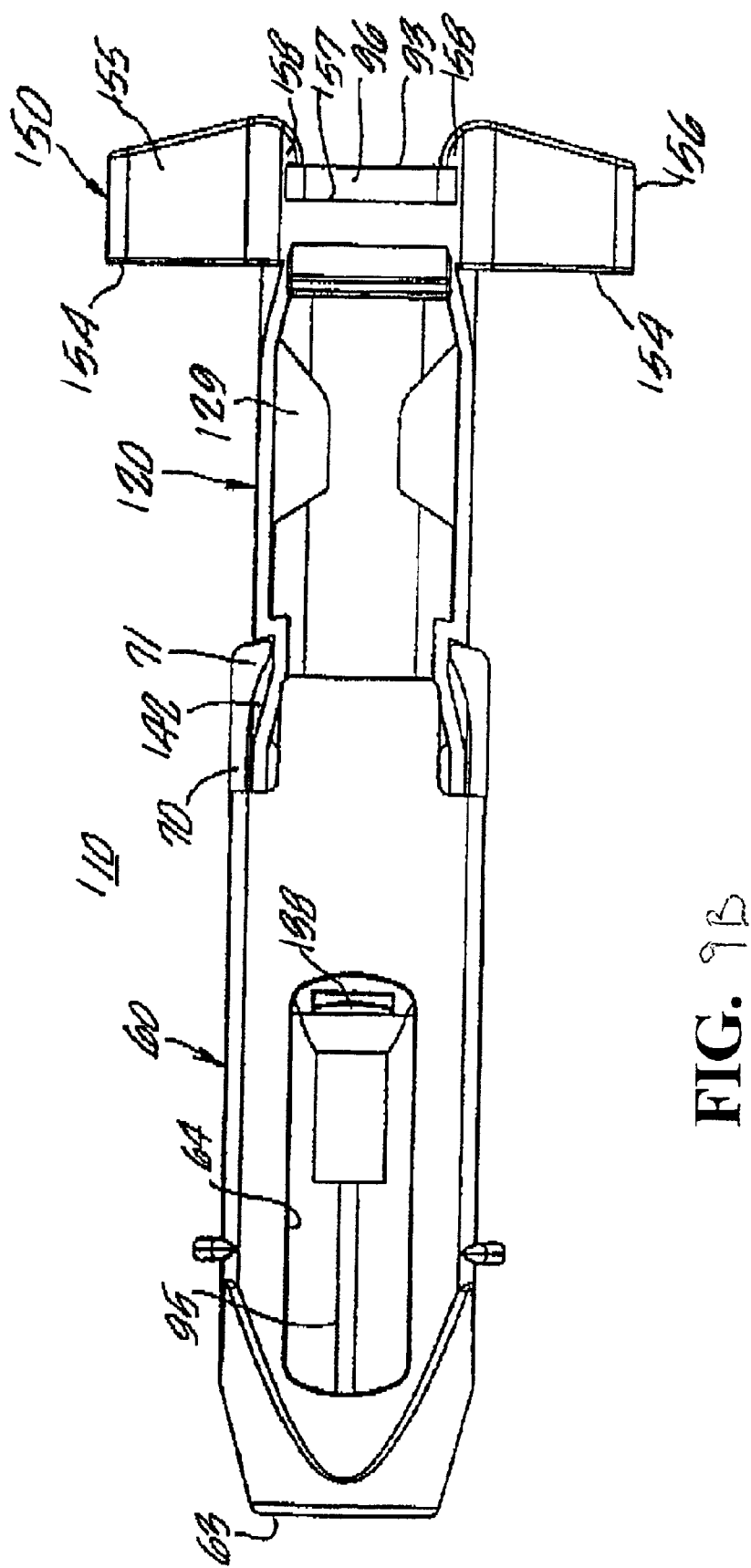

With particular reference to FIGS. 9A and 9B, a relatively small syringe 90, e.g., a 0.5 mL pre-filled syringe, may be inserted into the body 120, the syringe 90 including a rigid needle protector cap 97 or similar safety cap having a diameter larger than the barrel 92. When the syringe 90 is directed distally into the proximal end 122 of the body 120, the needle protector cap 97 may engage the ribs 29 as it enters the cavity 126. Because of the semi-rigid nature of the ribs 129, for example, due to inherent resilience of injection molded plastic, the ribs 129 may be deflected outwardly and/or away from one another to accommodate the needle protector cap 97 as it passes distally through the cavity 126.

Alternatively, the ribs 129 may be substantially rigid and the side rails 128 themselves may be sufficiently flexible to deform outwardly as the needle protector cap 97 engages the ribs 129 to allow the cap 97 to pass distally through the cavity 126. In such an embodiment, however, the pre-filled syringe 90 may have to be inserted into the body 120 before directing the shield 60 onto the body 120, or the shield 60 may have to be sufficiently flexible and resilient to accommodate the expansion of the rails 128.

Once the needle protector cap 97 extends beyond the distal end 124 of the body 120, the ribs 129 may resiliently return to abut or engage the barrel 92 of the pre-filled syringe 90, thereby preventing substantial lateral movement of the pre-filled syringe 90 within the guard 110 during use. The ribs 129 may engage the barrel 92 to enhance the rigidity of the body 120, i.e., to prevent the rails 128 from being deflected inwardly, which may release detents 142, 71 on the body 120 and/or shield 60, and consequently, release the shield 60 from the guarded position. For example, as can be seen in FIGS. 7C–D, the barrel 92 of the syringe 90 has a diameter smaller than the cross-section of the cavity in the body 120. After using the syringe 90, as described previously, the shield 60 may be directed distally to the guarded position, wherein the detents 71 engage the detent pockets 142 to prevent proximal movement of the shield 60, which may otherwise expose the used needle 95.

Optionally, the body 20 may include one or more deflectable tabs (not shown), such as those described above, which may be deflected inwardly to contact the barrel 92 of the syringe 90 after the syringe 90 is inserted into the cavity 126.

Figure 10:
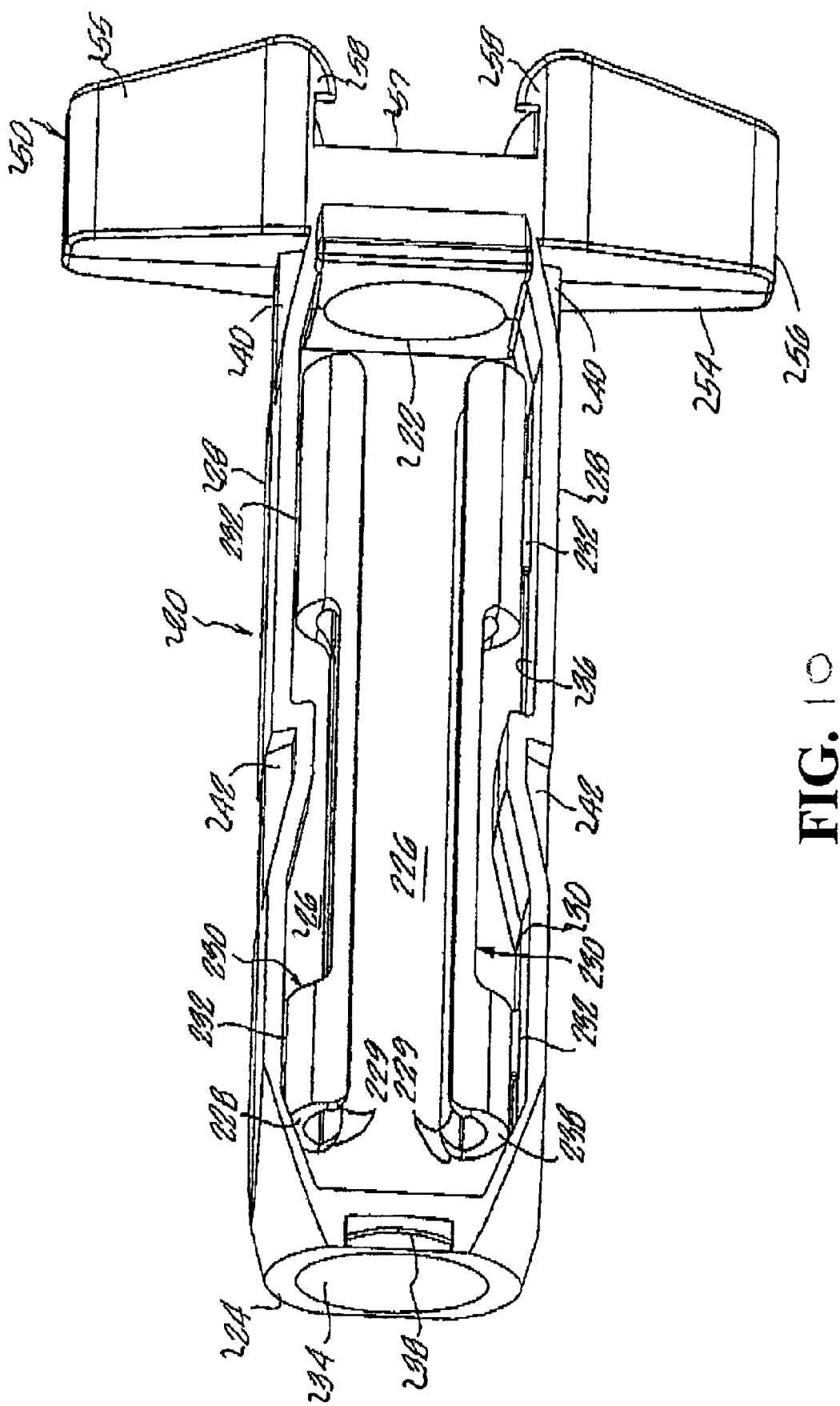
FIG. 10 is a perspective view of another alternative embodiment of a body for a syringe guard.
Figure 11:
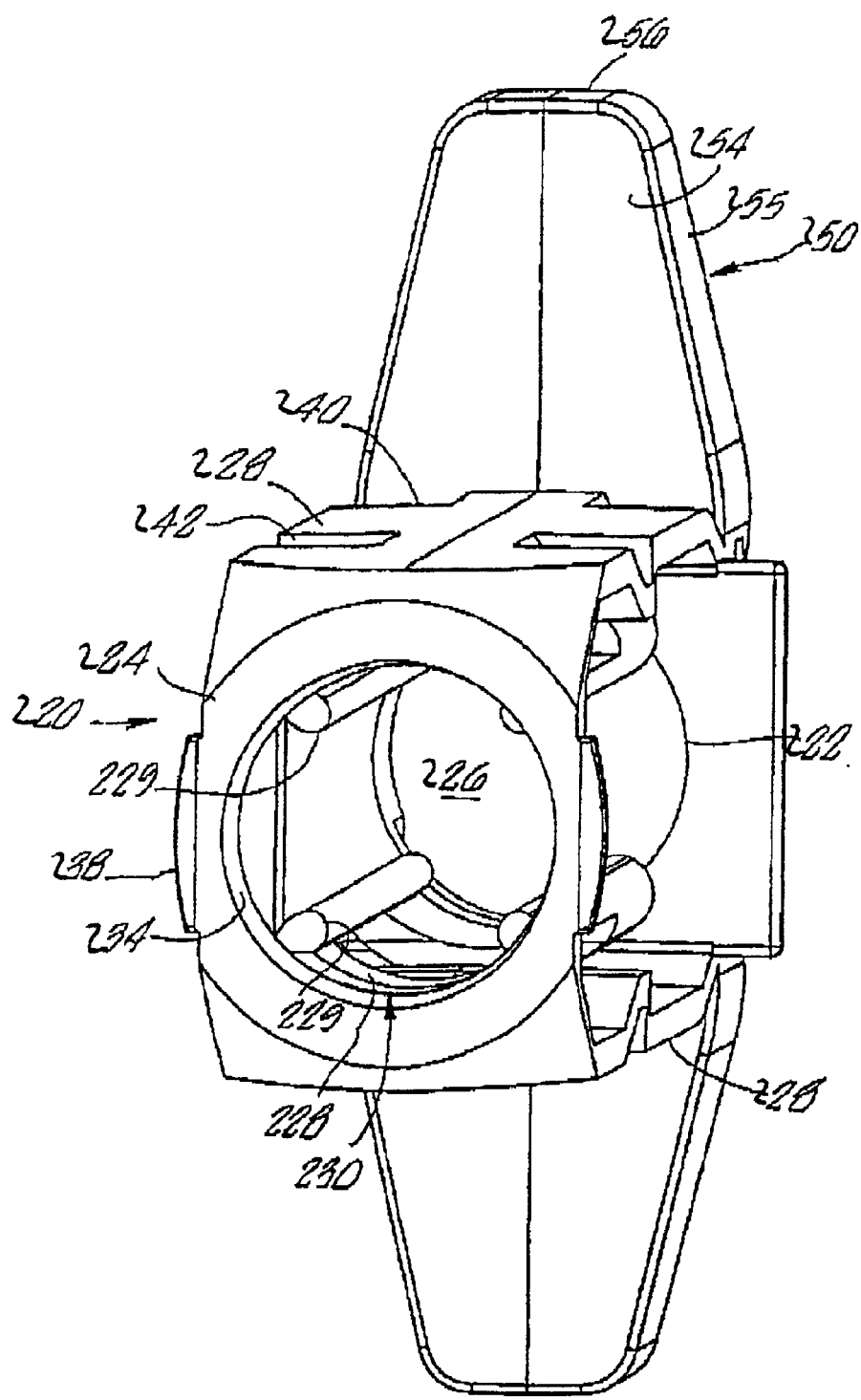
FIG. 11 is a perspective view of yet another alternative embodiment of a body for a syringe guard.

Alternatively, as shown in FIGS. 10 and 11, the body 220 may include a deflectable cradle or frame 230 for supporting the ribs 229. Preferably, the frame 230 has arms 228 with a curved or semi-circular cross-section defining an inner cavity 226 similar in shape and size to the barrel of the small unit dose pre-filled syringe (not shown) to be received therein. The frame 230 is attached or molded to the rails 228 by one or more support legs or tabs 232. The ribs 229 are then formed along at least a portion of the frame 230, preferably extending between two frames 230 as shown. The ribs 229 may have a tapered, rounded, or other cross-section for engaging the barrel and/or the needle cap of a syringe.

The deflectable, resilient nature of the frame 230 may facilitate inserting a syringe being received in the body 220. The arms 228 on the frame 230 may be deflected outwardly to accommodate a needle protector cap, but resiliently return to engage the barrel with the ribs 229, thereby providing additional rigidity for the rails 228, as described above.

Turning to FIGS. 12A and 12B, another embodiment is shown that includes a guard 310, similar to any of the embodiments disclosed in U.S. Pat. Nos. 6,030,366, 6,159,184, or application Ser. Nos. 09/566,224 and 09/724,657, incorporated by reference above. Generally, the guard 310 includes a body 320 including proximal and distal ends 322, 324, and a cavity 326 extending therebetween. A shield 360 is slidably attached to the body 320, which may be manually or automatically advanceable from an unguarded position (shown in FIG. 12B) to a guarded position (not shown). The body 320 may include a finger grip 350 and/or a locking mechanism, such as detents 358, for substantially permanently encapsulating a syringe 90 within the body 320. The body 320 and shield 360 may also include cooperating detents (not shown), similar to those described above, for holding and/or locking the shield 360 in the unguarded and guarded positions.

The guard 310 is intended to be used with a syringe 90 that includes a barrel 92, a needle 95 extending from a distal end 94 of the barrel 92, and a needle protector cap 97 detachably covering the needle 95. Generally, the barrel 92 has an outer diameter or other cross-section that is substantially smaller than an outer diameter or cross-section of the needle protector cap 97. The cavity 326 of the body 320 has a sufficiently larger diameter or cross-section for receiving the needle cap 97 therethrough as the syringe 90 is being received in the body 320, as shown in FIGS. 12A, and similar to the embodiments described above.

In addition, the guard 310 includes an annular collar 380 provided on the barrel 92 of the syringe 90, as shown in FIG. 13. The collar 380 generally defines an outer diameter that is as large or larger than the diameter of the needle protector cap 97. Preferably, the collar 380 has an outer diameter that is smaller than the diameter of the cavity 326 in the body 320 such that the collar 380 may be slidably received in the cavity 326, yet with relative lateral stability. Alternatively, as shown in FIG. 14, other radial elements may be provided on the barrel 92 of the syringe 90, for example, a plurality of radial tabs 380.' Preferably, at least three radial tabs 380' may be provided, thereby ensuring that the barrel 92 is substantially supported in any lateral direction. The radial element may have a length that is substantially less than a length of the barrel 92, or the radial element may extend along a substantial length or the entire length of the barrel 92.

The collar 380, tabs 380,' or other radial element(s) may be separately formed, e.g., from plastic, and attached or otherwise secured to the barrel 92. For example, the collar 380 may be secured by mechanical interference or other frictional engagement. In addition or alternatively, the radial element(s) may be attached to the barrel 92 using an adhesive and/or by melting or otherwise fusing the radial element(s) to the barrel 92. In a further alternative, the radial element may be integrally molded, e.g., from glass, as part of the barrel 92. In yet a further alternative, a collar may be provided that has a "C" shape (not shown) that may be fitted around the barrel. The "C" shaped collar may have an inner diameter that is slightly smaller than the outer diameter of the barrel 92. The "C" shaped collar may be expanded as it is inserted over the barrel 92, but may remain biased towards its initial diameter to enhance frictional engagement with the barrel 92, either alone or in addition to an adhesive.

Once the syringe 90 is securely received in the body 320, the radial element(s) on the barrel 92 may define an outer diameter sufficient for contacting a side wall or rail 328 of body 320 to prevent substantial lateral movement of syringe 90. Thus, once the protector cap 97 is removed, e.g., to inject medication in the syringe 90 into a patient, the radial element(s) may provide lateral support, thereby preventing the needle 95 form moving laterally within the open distal end 324 of the body 320 during use. After use, the shield 360 may be advanced over the needle 95 and substantially locked in the guarded position to facilitate safe disposal and/or prevent reuse, similar to the embodiments described above.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. An injection device comprising:
    a syringe comprising a barrel for containing medicine, the barrel having proximal and distal ends, a needle extending from a distal end of the barrel, and a needle protector cap detachably covering the needle;
    a radial element extending from the barrel comprising a collar intermediate the proximal and distal ends of the barrel;
    a body comprising open proximal and distal ends, and a cavity extending between the proximal and distal ends of the body for receiving the syringe therein, the cavity having a cross-section for receiving the needle protector cap therethrough as the syringe is inserted into the cavity, the collar contacting an inside surface of the body for preventing substantial lateral movement of the syringe within the cavity, the needle and needle protector cap at least partially extending beyond the distal end of the body when the syringe is received in the cavity;
    a shield slidably attached to the body, the shield having proximal and distal ends, the distal end of the shield having an opening through which the needle and the needle protector cap extend when the shield is in an unguarded position, the shield being slidabie between the unguarded position and a guarded position wherein the needle is covered by the shield; and
    one or more detents on the shield for locking the shield in the guarded position.

2. The injection device of claim 1, wherein the radial element is integrally molded as part of the barrel.

3. The injection device of claim 1, wherein the radial element is a substantially annular collar having an outer diameter approximately as large as an outer diameter of the needle protector cap.

4. The injection device of claim 3, wherein the collar is secured to the barrel by at least one of mechanical interference and an adhesive.

5. The injection device of claim 3, wherein the collar is integrally molded as part of the barrel.

6. The injection device of claim 1, wherein the radial element comprises a "C" shaped collar.

7. The injection device of claim 1, further comprising a locking mechanism on the proximal end of the body, the locking mechanism engaging a proximal end of the syringe to limit axial movement of the syringe.

8. The injection device of claim 7, wherein the locking mechanism comprises one or more detents defining a slot, the slot receiving at least a portion of a flange on the proximal end of the barrel therein to substantially secure the syringe within the cavity.

9. The injection device of claim 1, wherein the syringe is a pre-filled syringe including medication therein.

10. An injection device, comprising:
    a syringe comprising a barrel for containing medicine, the barrel having proximal and distal ends, a needle extending from a distal end of the barrel, and a needle protector cap detachably covering the needle;
    a radial element extending from the barrel comprising a plurality of tabs intermediate the proximal and distal ends of the barrel;
    a body comprising open proximal and distal ends, and a cavity extending between the proximal and distal ends for receiving the syringe therein, the cavity having a cross-section for receiving the needle protector cap therethrough as the syringe is inserted into the cavity, the tabs contacting an inside surface of the body for preventing substantial lateral movement of the syringe within the cavity, the needle and needle protector cap at least partially extending beyond the distal end of the body when the syringe is received in the cavity; and
    a shield slidably attached to the body, the shield having proximal and distal ends, the distal end of the shield having an opening through which the needle and the needle protector cap extend when the shield is in an unguarded position, the shield being slidable between the unguarded position and a guarded position wherein the needle is covered by the shield; and one or more detents on the shield for locking the shield in the guarded position.

11. The injection device of claim 10, wherein the plurality of tabs are disposed circumferentially about the barrel.

* * * * *